(12) United States Patent
Stone et al.

(10) Patent No.: US 6,533,797 B1
(45) Date of Patent: Mar. 18, 2003

(54) CONTROL GRIP ASSEMBLY

(75) Inventors: Corbett W. Stone, San Diego, CA (US); Nicolei R. King, San Diego, CA (US); Robert S. Lynch, San Diego, CA (US); James F. Marino, La Jolla, CA (US)

(73) Assignee: NuVasive, San Diego, CA (US)

( * ) Notice: Subject to any disclaimer, the term of this patent is extended or adjusted under 35 U.S.C. 154(b) by 143 days.

(21) Appl. No.: 09/717,839

(22) Filed: Nov. 21, 2000

Related U.S. Application Data

(60) Provisional application No. 60/167,415, filed on Nov. 24, 1999.

(51) Int. Cl.⁷ ................................................. A61B 7/84
(52) U.S. Cl. .......................... 606/184; 606/1; 606/169
(58) Field of Search .............................. 606/1, 51, 52, 606/205–210, 169, 139, 142; 600/562–568

(56) References Cited

U.S. PATENT DOCUMENTS

| | | | |
|---|---|---|---|
| 5,370,658 A | * | 12/1994 | Scheller et al. |
| 5,383,895 A | * | 1/1995 | Holmes et al. |
| 5,501,698 A | * | 3/1996 | Roth et al. |
| 5,618,306 A | * | 4/1997 | Roth et al. |

* cited by examiner

*Primary Examiner*—Francis J. Jaworski
*Assistant Examiner*—Maulin Patel
(74) *Attorney, Agent, or Firm*—Jonathan Spangler

(57) ABSTRACT

A control handle assembly, comprising, a body; a pair of handles extending from the body; and an actuator disposed within the body, wherein the handles move in unison, and wherein movement of the actuator is controlled by movement of the pair of handles.

3 Claims, 14 Drawing Sheets

CONTROL GRIP ASSEMBLY

CROSS-REFERENCES TO RELATED APPLICATIONS

This application claims the benefit of prior provisional application No. 60/167,415 filed Nov. 24, 1999, the full disclosure of which is incorporated herein by reference.

The present invention relates to control grip handles on surgical instruments, and especially to control grip handles on rongeurs, suction punches and articulators.

BACKGROUND OF THE INVENTION

Typically, a "pistol grip" control handle is used to open and close a cutting blade on a rongeur or suction punch. Such "pistol grip" control handles are also commonly used to control the degree of curvature or to control jaw movement of an articulating instrument.

Unfortunately, existing "pistol grip" control handles are somewhat cumbersome to use as they provide only a single way in which an operator's hand can grip them. Pistol grips are especially cumbersome to use when the body of the surgical instrument is quite long and the surgical instrument is positioned at an awkward angle to the surgeon. This is especially true when an elongated surgical instrument such as a rongeur, suction punch or articulating instrument is inserted through a long cannula into the patient. Since the cannula faces downwardly into the patient, the operator is forced to grasp the instrument's pistol grip at an awkward angle, requiring the surgeon to excessively rotate their wrist to grasp the downwardly facing pistol grip. Moreover, when reaching long distances, such as is required when inserting elongated surgical instruments through an elongated cannula, it is typically difficult to precisely control the movement of the pistol grip handle.

SUMMARY OF THE INVENTION

The present invention provides a control grip assembly for controlling the operation of an actuator in a surgical instrument and is particularly well-suited for controlling longitudinal movement of a cutting blade in a suction punch or rongeur, angular movement of an articulator, or controlling the opening and closing of the jaws of an articulator.

The present invention provides a control handle assembly comprising a body having a pair of handles extending therefrom. The handles each extend from opposite sides of the body and preferably move together in unison such that squeezing of the handles by the surgeon controls the positioning of an actuator disposed within the body. Movement of the actuator, (caused by movement of the handles), can be used to control the motion or operation of a surgical instrument. For example, movement of the actuator can be used to open and close a cutting blade on a rongeur or suction punch, or to control the degree of curvature or jaw movement of an articulator.

In a preferred embodiment, the present invention comprises a body having a pair of outwardly extending handles wherein each handle extends from opposite sides of the body, with the distal ends of the handles being pivotally connected to the body. Within the interior of the body, a pair of struts are positioned with each strut being pivotally connected to one of the handles. A axially displaceable actuator mechanism is also disposed within the body. Movement of the handles causes the struts to move which in turn causes axial displacement of the axially displaceable actuator mechanism.

In a preferred aspect of the invention, each strut is connected to a handle near or at the mid-section of the handle. As such, a fulcrum effect occurs since the pivot point for connection of the handle to the body is preferably found at the distal end of the handle.

An important advantage of the present actuator grip assembly is that an operator can use a "dagger" grip on the assembly, (i.e., holding an elongated assembly with the operator's thumb pointing in a proximal direction away from the "operating" distal end of the device), during its operation as opposed to a traditional "pistol" grip in which the operator must point their hand in a distal direction, typically with their thumb perpendicular to the elongated body of the instrument.

Advantages of the present grip assembly include the fact that it is "left and right reversible", (i.e., an operator may easily, and interchangeably, grip and operate it with either their left or right hand).

The present grip assembly is also "top and bottom reversible", (i.e., an operator may easily, and interchangeably, grip and operate it from either the top or bottom side).

The present grip assembly is also "front and back reversible". Specifically, although an advantage of the present invention is that an operator can operate the device while pointing their thumb in the proximal direction, an operator may also operate the device while pointing their thumb in the distal direction.

Being "left and right", "top and bottom" and "front and back" reversible provides numerous advantages. For example, an operator is able to easily grasp the device from any direction, using the most convenient grasp possible. Accordingly, should the operator be moving around the patient during a surgical procedure, or otherwise altering their orientation with respect to that of the patient over time, the operator is free to grasp the present control grip assembly from any direction. An additional benefit of the present control grip assembly is that the operator is free to change the positioning of their hand on the assembly over time, thereby avoiding fatigue.

Consequently, advantages of using the present "dagger" grip as opposed to a conventional "pistol" grip are that the dagger grip is easier to work with, being steadier when the operator is moving their hands about.

An additional advantage of the present invention is that, in a preferred aspect, the body of the device is shaped to itself be easily grasped in the operator's palm. As such, both the body, and the pair of handles expending therefrom is shaped to be easily grasped in the operator's palm, providing a secure, comfortable grip on the assembly.

DESCRIPTION OF THE SPECIFIC EMBODIMENTS

Figure 1:
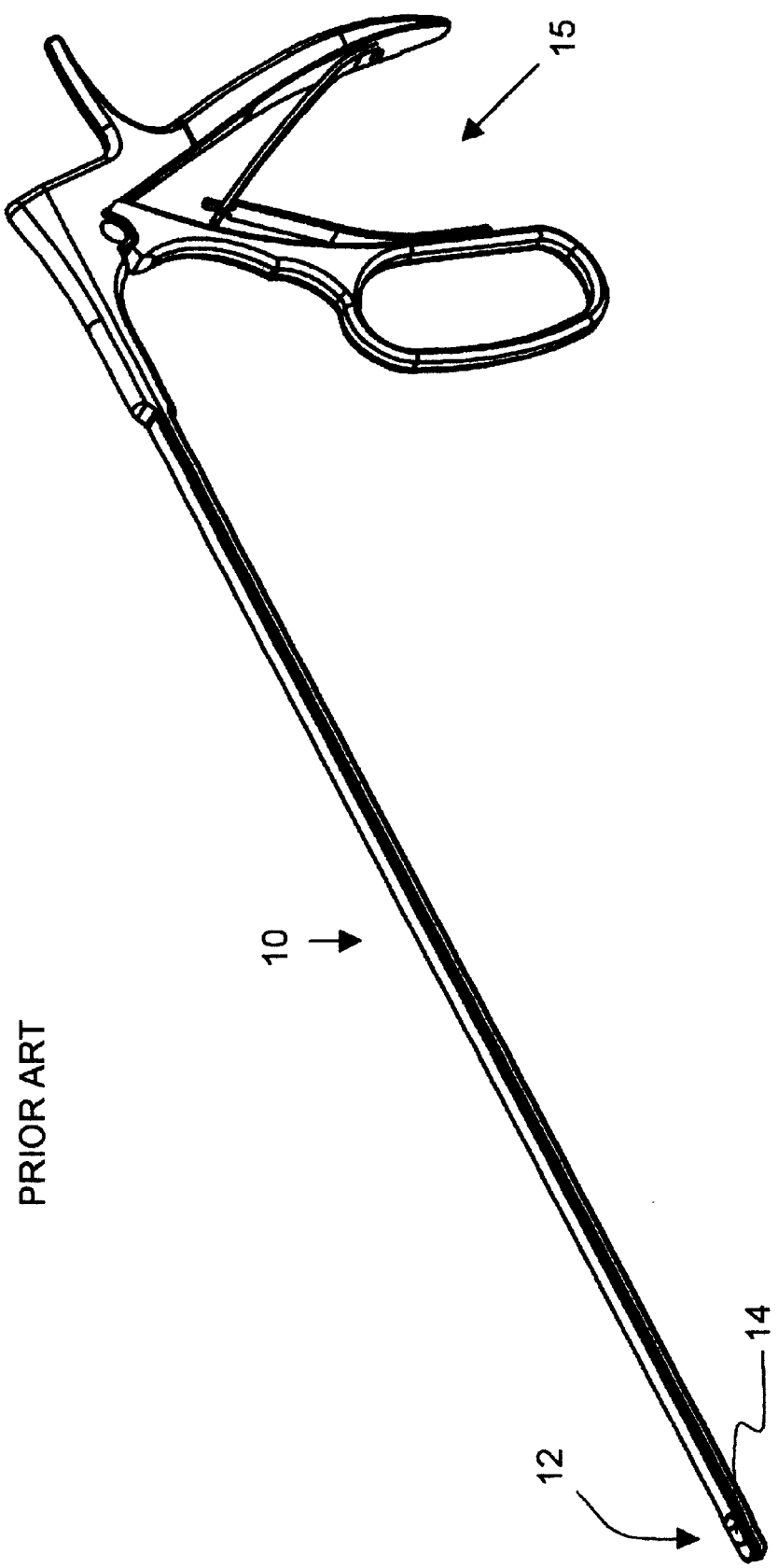
FIG. 1 is an illustration of a conventional surgical rongeur.

FIG. 1 is an illustration of a typical surgical rongeur 10 having a side opening 12 with an internal cutting blade 14. The internal cutting blade 14 is moved axially by squeezing pistol grip 15.

Figure 2:
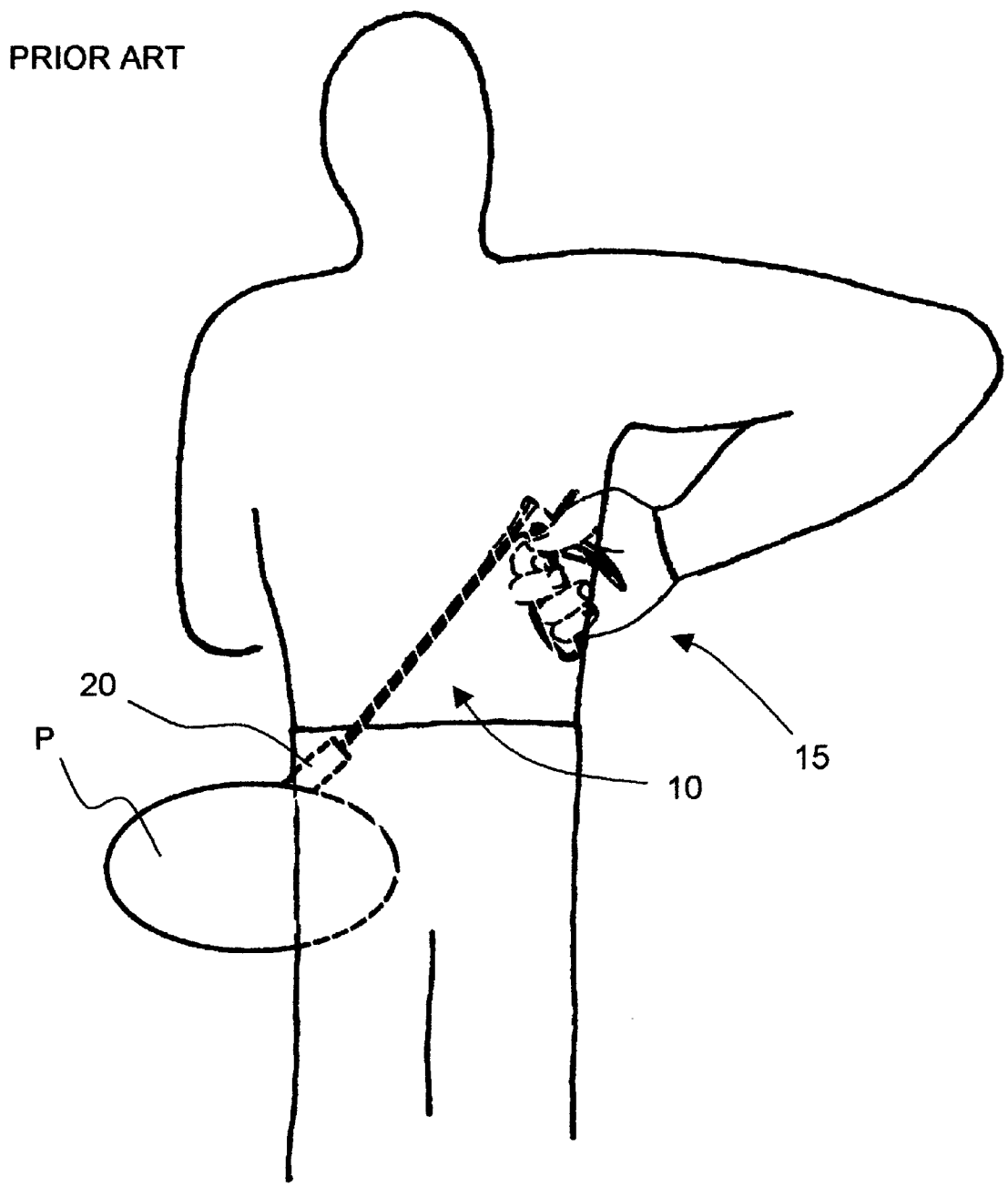
FIG. 2 is an illustration of an operator holding the surgical rongeur of FIG. 1 when the rongeur is introduced in a cannulated posterolateral approach into a patient.

FIG. 2 shows an operator holding the rongeur of FIG. 1 in a cannulated posterolateral approach into a patient with rongeur 10 received into cannula 20 which is posterolaterally inserted into patient P. As can be seen in FIG. 2, a disadvantage of conventional pistol grip 15 is that the operator is forced to considerably extend their arm and rotate their wrist such that pistol grip 15 can be held with the operator's hand pointing downwardly in a distal direction.

Figure 3:
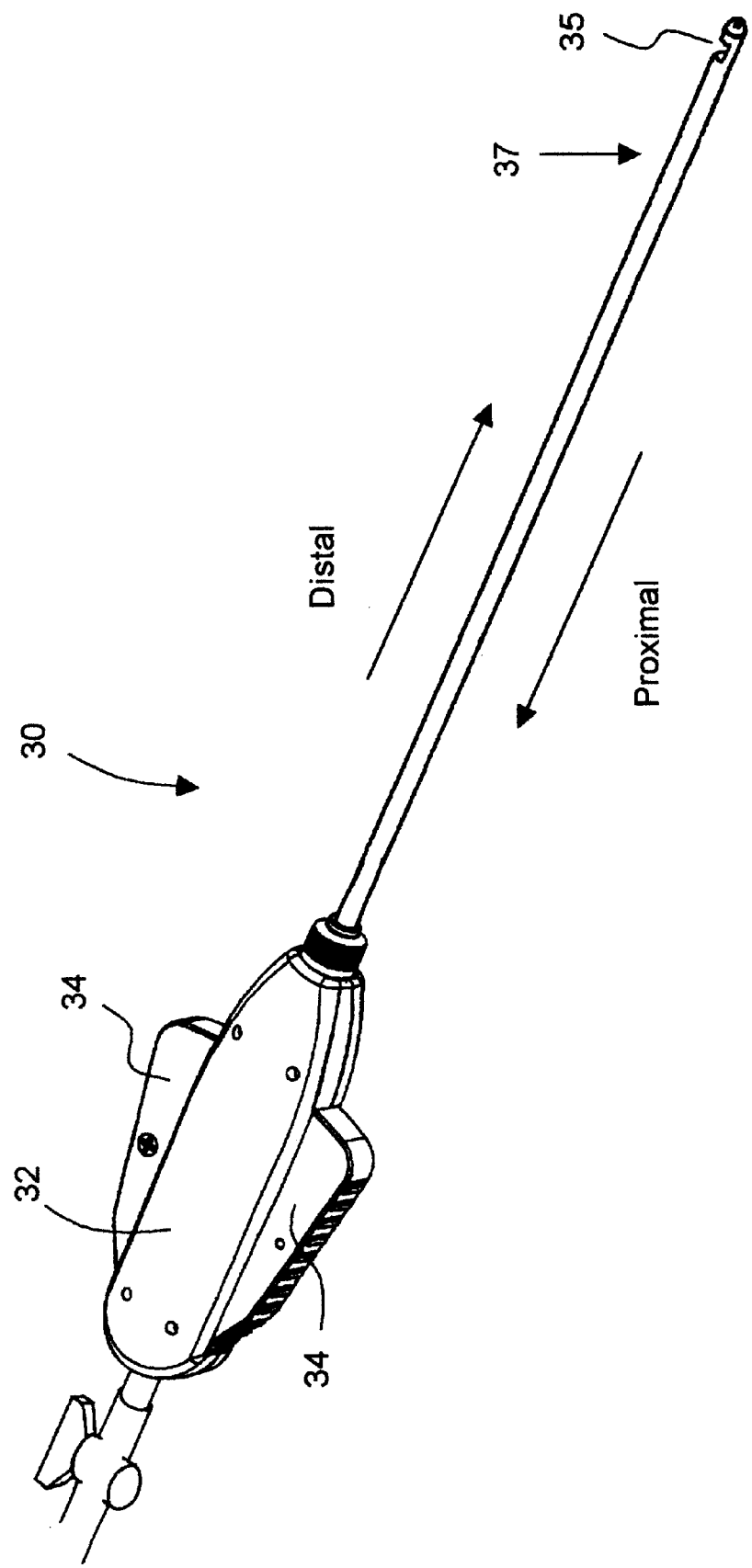
FIG. 3 is a perspective view of the present invention.

As seen in FIG. 3, the present invention provides a novel control grip assembly 30, comprising a body 32 and a pair of handles 34 which when squeezed together in unison control the actuation of an axially displaceable actuator mechanism. Such actuator mechanism may, for example, control the movement of a cutting blade 35 in a rongeur tube 37, as shown.

Figure 4:
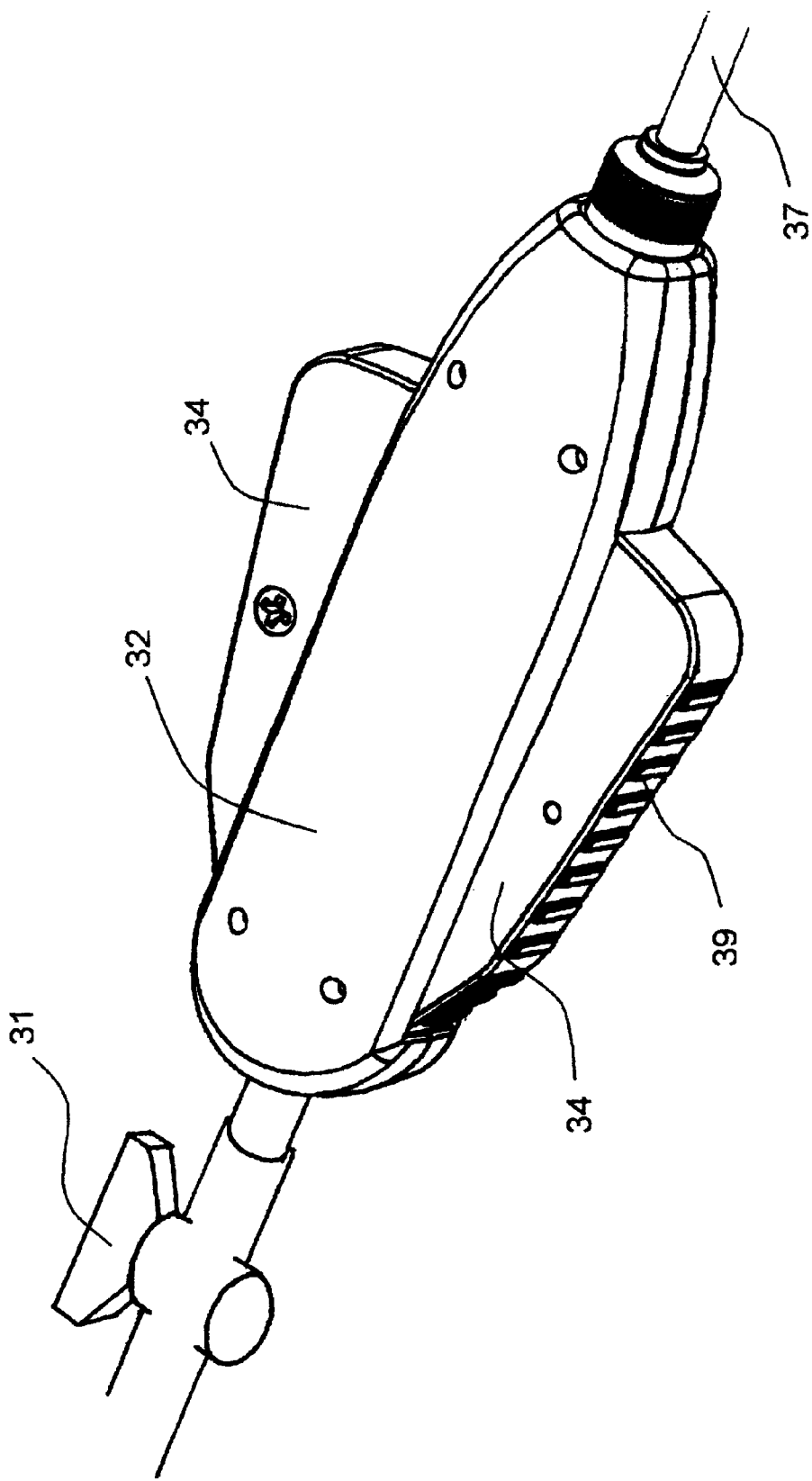
FIG. 4 is a close-up perspective view corresponding to FIG. 3.

As seen in FIG. 4, each of handles 34 may optionally have a series of traction grooves or protrusions 39 disposed along their outer perimeter. An optional valve 31 may be used to control a suctioning air flow through rongeur tube 37. When assembly 30 is held by the operator with their thumb facing in a proximal direction, the operator can use their thumb to control the operation of valve 31.

Figure 5:
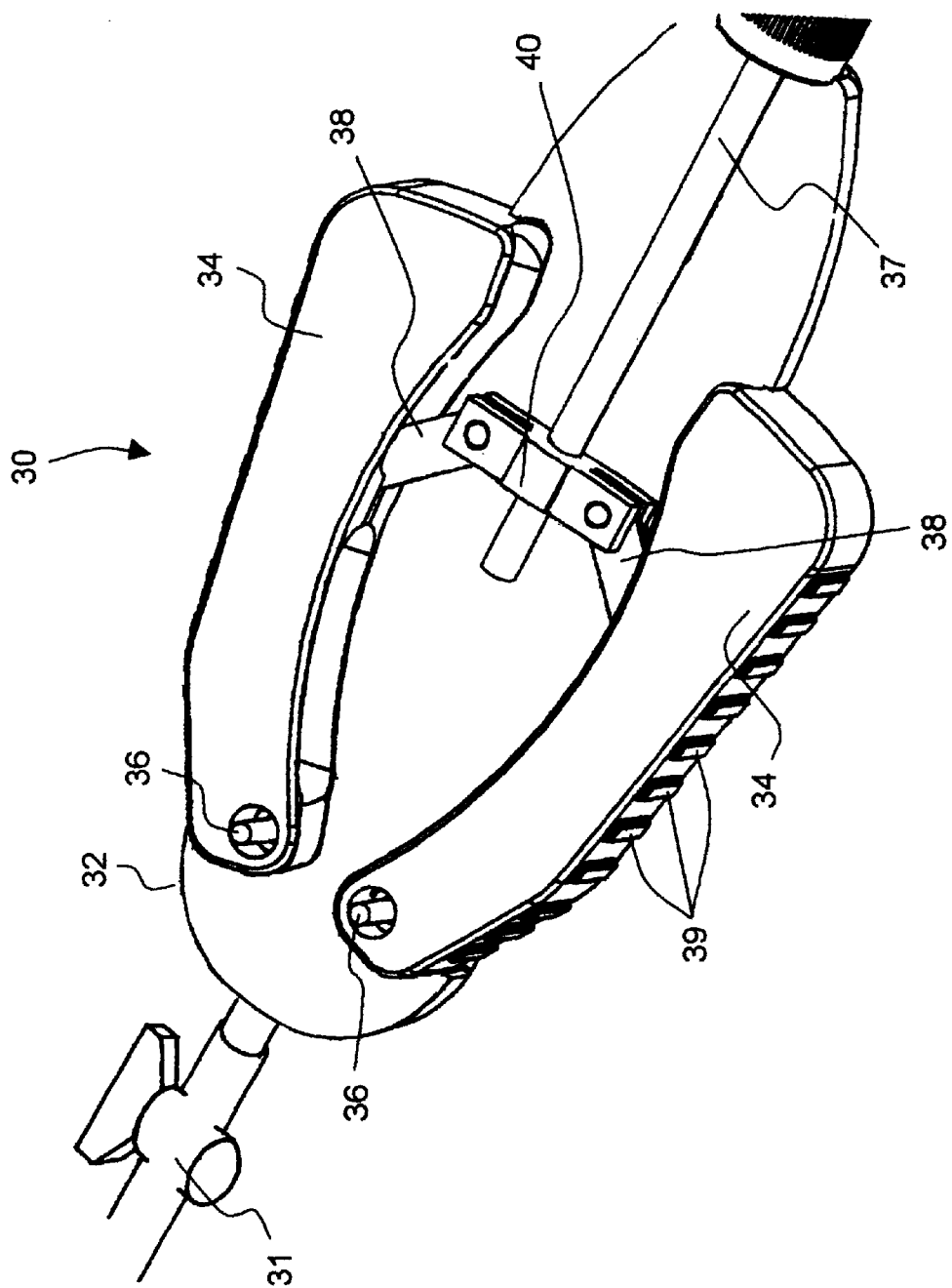
FIG. 5 is a sectional view of the invention corresponding to FIGS. 3 and 4.
Figure 11:
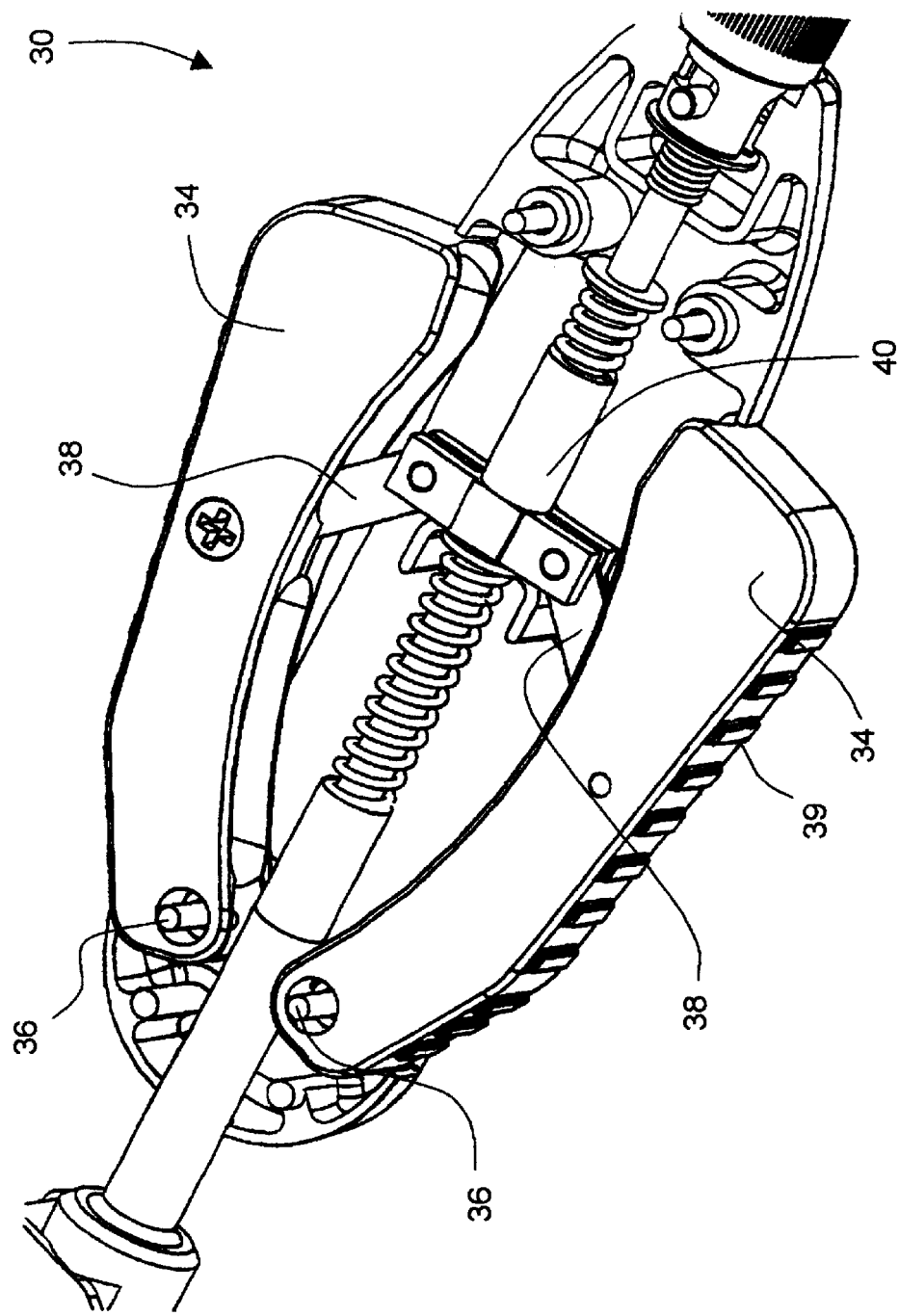
FIG. 11 is a cut-away view of the present invention.

Referring to FIGS. 5 and 11, further details of the interior of grip assembly 30 are shown. Each of handles 34 are pivotally connected at points 36 to the frame of body 32. In a preferred aspect, handle 34 is connected with pivot point 36 being disposed at the proximal end of the handle. A strut 38 connects handle 34 to actuator controller 40. Actuator controller 40 preferably is adapted to slide axially within body 32.

Accordingly, squeezing together handles 34 will cause actuator controller 40 to be displaced in an axial direction. The displacement of the axial controller can be used either to control operation of a wide variety of surgical instruments. For example, axial movement of actuator controller 40 can control the articulation of an articulating arm, or the axial displacement of a cutting blade in a surgical rongeur or suction punch as shown.

Figure 6:
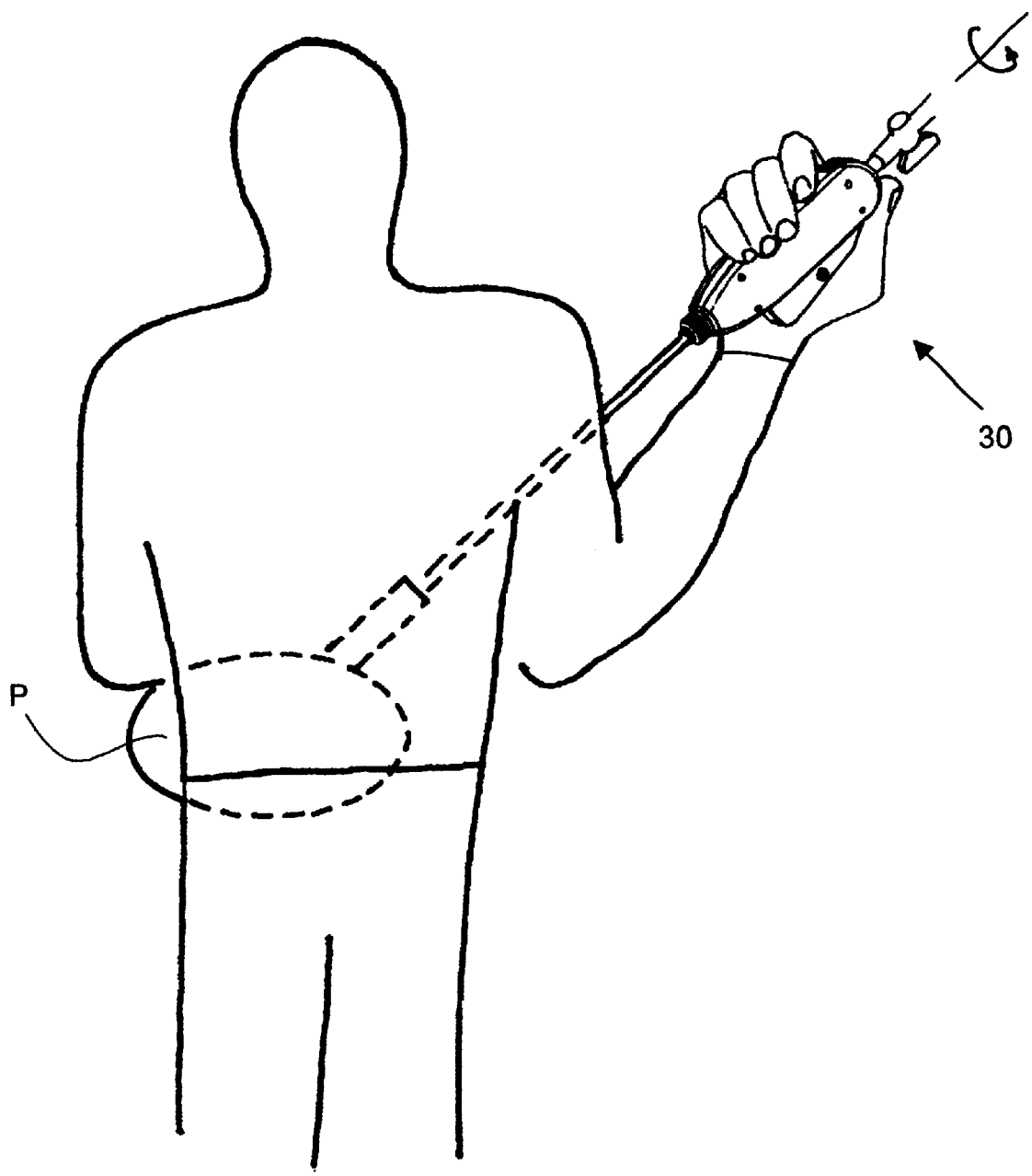
FIG. 6 shows an operator using the present invention in a cannulated posterolateral approach.

FIG. 6 shows the advantages of using the present invention when operating in a cannulated posterolateral approach. Specifically, the operator can grasp control grip assembly 30 in a "dagger" type grip, holding handles 34 in the palm of their hand, with their thumb pointed in a proximal direction relative to the device, (i.e., away from the "operating" distal end of the instrument), thus preventing excessive turning of their wrist to an uncomfortable position, as was shown with the conventional pistol grip seen in FIG. 2. The actuator grip assembly 30 can optionally be rotated in direction R by 180° such that it is possible to grasp the device from either side, using the same hand.

Figure 7A:
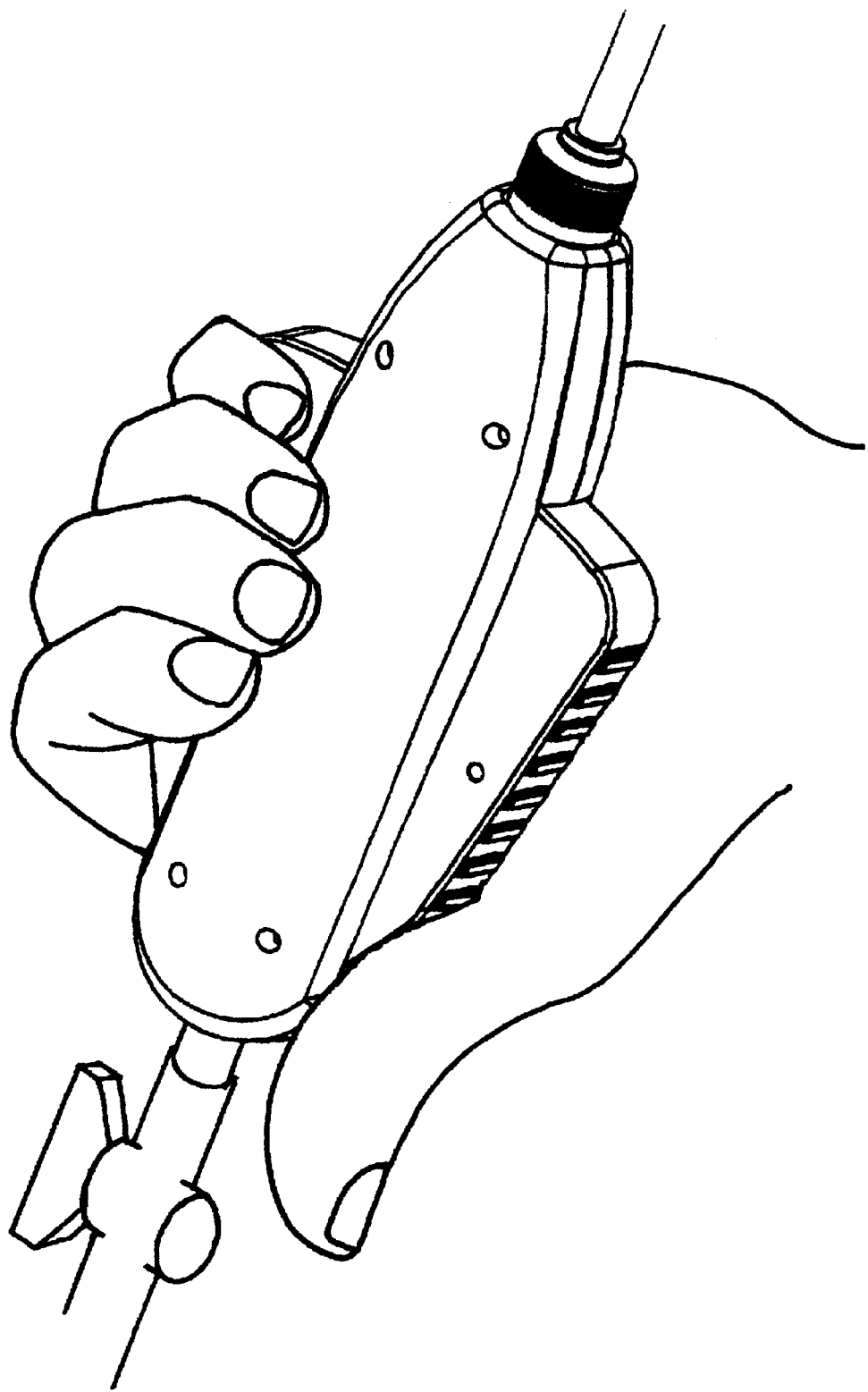
FIG. 7A shows an operator's left hand holding the invention with the thumb pointed in a proximal direction.
Figure 7B:
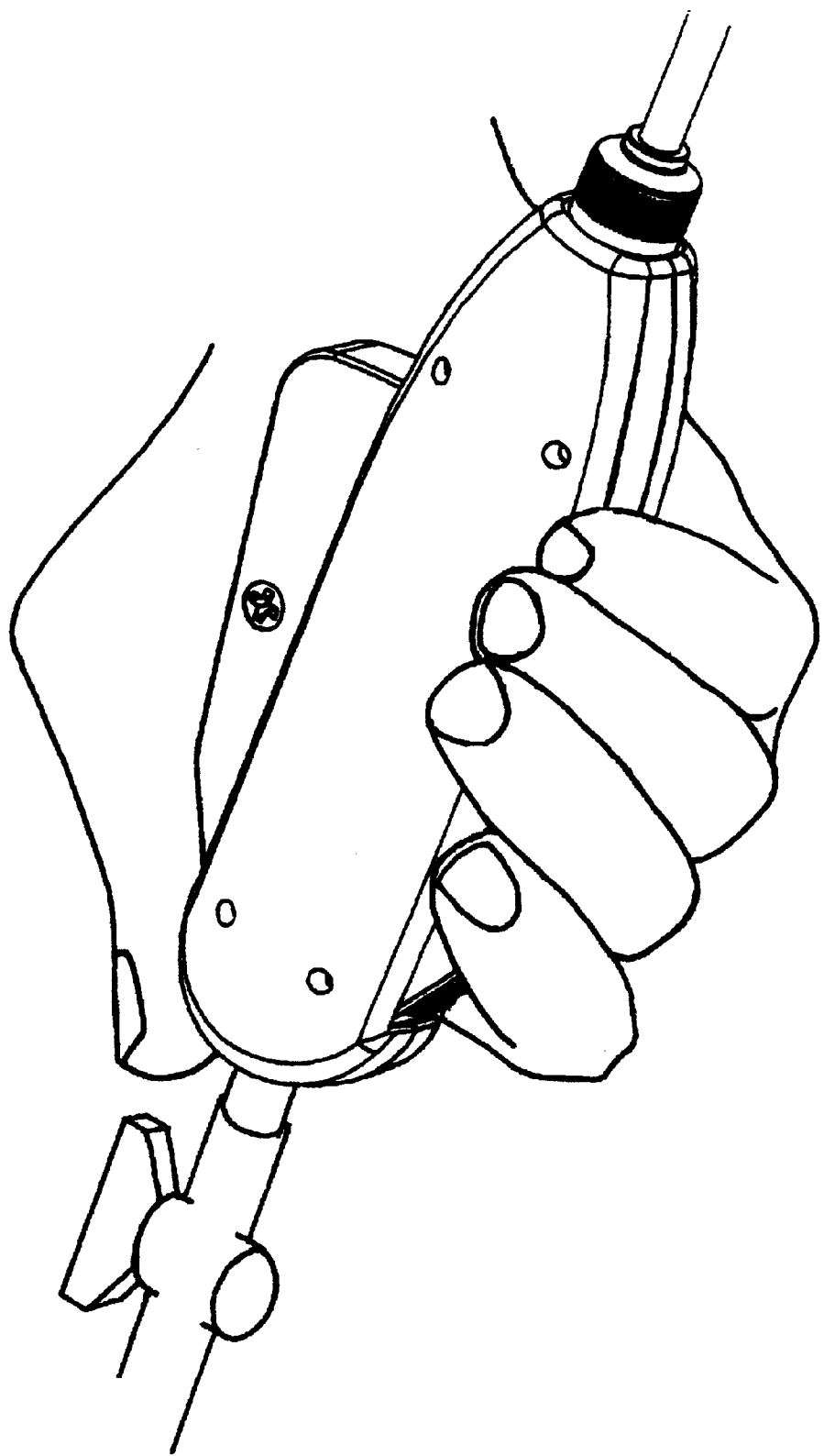
FIG. 7B shows an operator's right hand holding the invention with the thumb pointed in a proximal direction.

FIGS. 7A to 7D illustrate further advantages of the present invention, showing the "left and right reversible", "front and back reversible" and "top and bottom reversible" nature of the invention. Specifically, as seen in FIG. 7A, the present control grip 30 can be conveniently held in an operator's left hand between the index finger and the thumb and/or the volar-radial aspect of the palm, with the thumb pointed in a proximal direction. Conversely, FIG. 7B shows a similar grip with the operator's right hand holding the invention with their thumb pointed in a proximal direction.

Figure 7C:
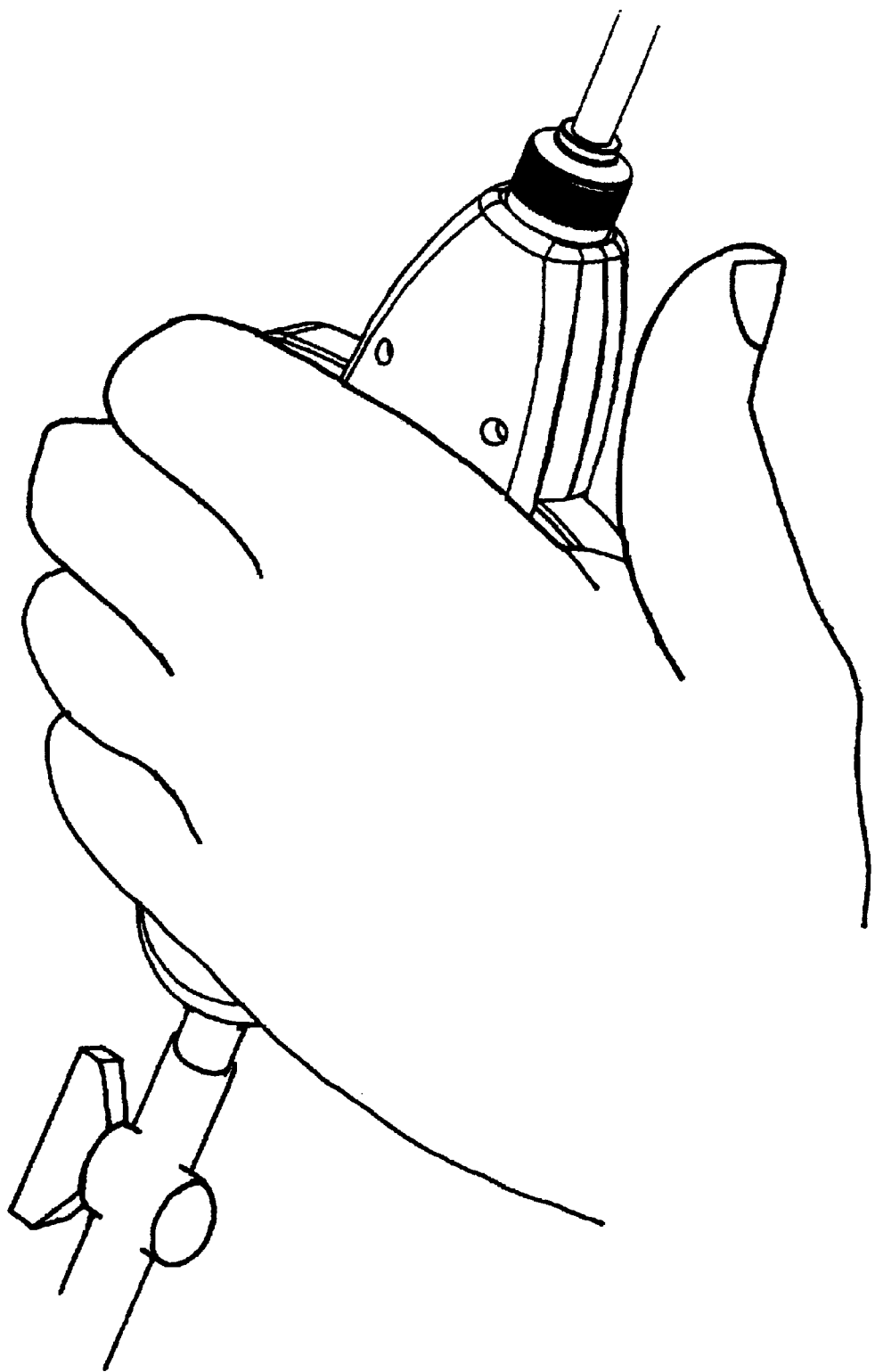
FIG. 7C shows an operator's left hand holding the invention with the thumb pointed in a distal direction.
Figure 7D:
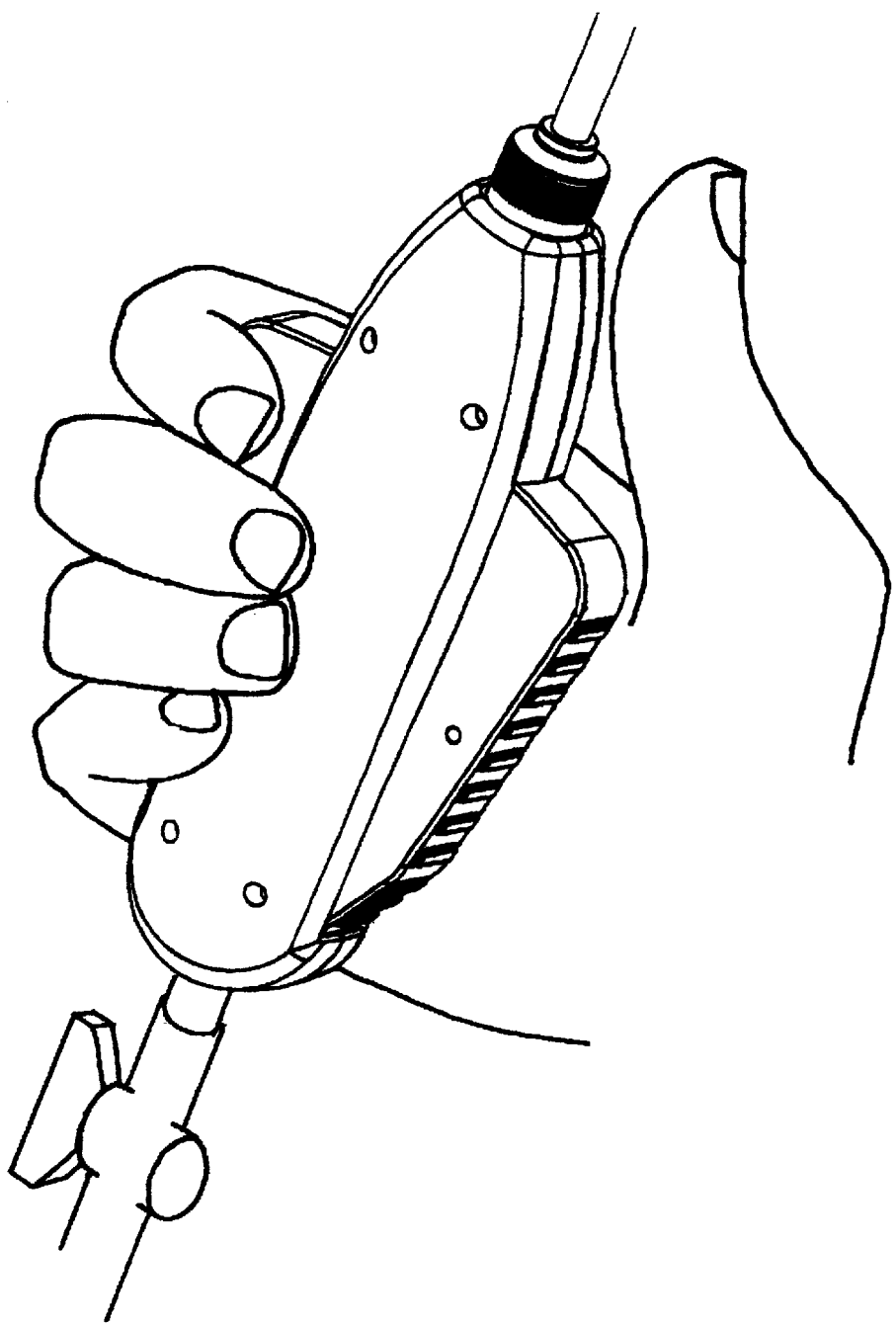
FIG. 7D shows an operator's right hand holding the invention with the thumb pointed in a distal direction.

FIG. 7C shows an operator's left hand holding the invention with the thumb pointed in a distal direction, (held between the little finger and the volar-ulnar aspect of the palm), and FIG. 7D conversely shows an operator's right hand holding the invention with the thumb pointed in a distal direction.

Figure 8:
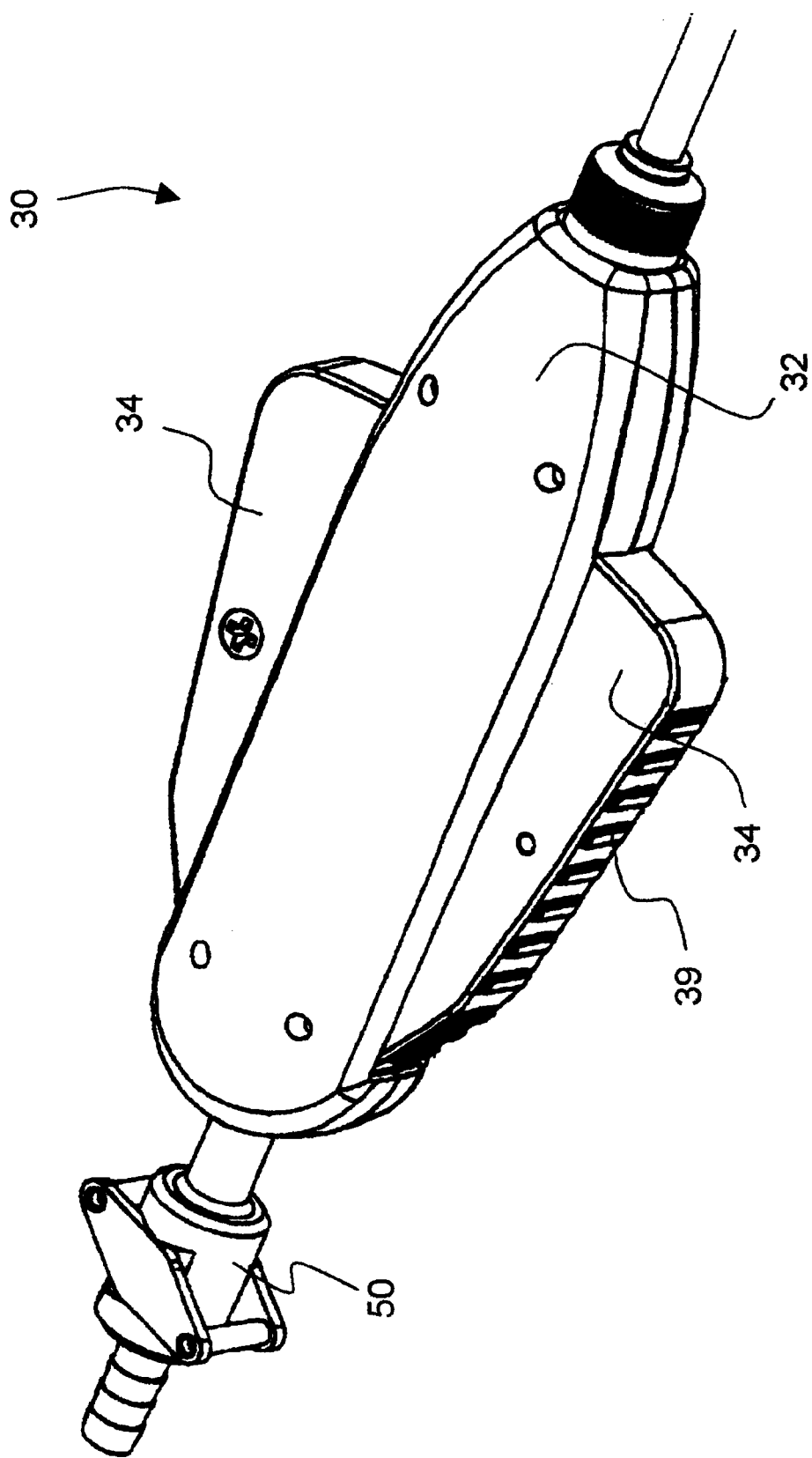
FIG. 8 is a perspective view of the invention, adapted for use on a suction punch.

FIG. 8 shows actuator grip assembly 30 outfitted with a valve 50, which may be controlled by the operator's thumb. In a preferred aspect, valve 50 opens and closes the suction punch.

Figure 9:
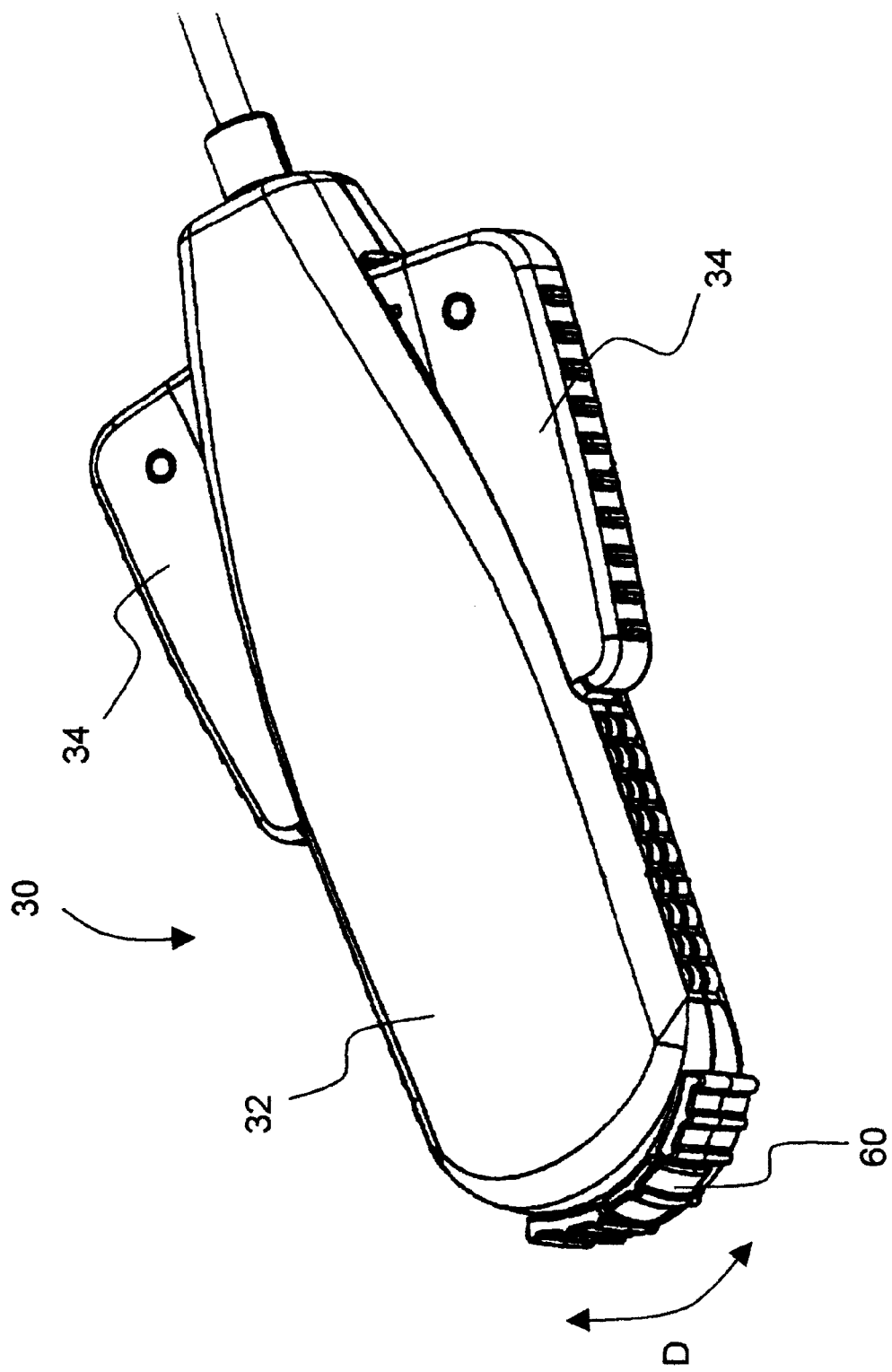
FIG. 9 is a perspective view of the invention, adapted for use in controlling the positioning and jaw movement of an articulator.
Figure 10:
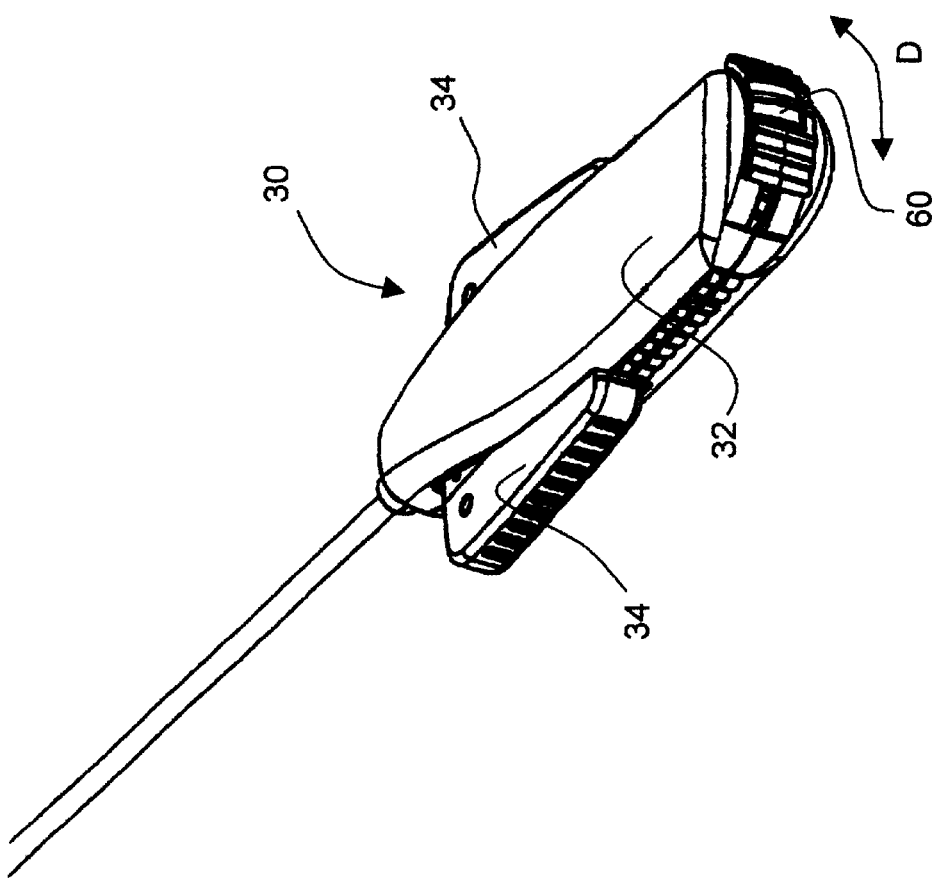
FIG. 10 is an additional view of the invention, adapted for use in controlling the positioning and jaw movement of an articulator.

FIGS. 9 and 10 show actuator grip assembly 30 outfitted with a slidable controller 60 which is movable back and forth in direction D. In a preferred aspect, the squeezing together of handles 34 operates to open and close jaws of an articulator, and the slidable positioning of controller 60 is used to control the degree of articulation of the articulator. Accordingly, an advantage of the present invention is that it permits one-hand control of both the opening and closing of articulator jaws and also the degree to which the articulator is angled.

What is claimed is:

1. A control grip assembly, comprising:

a body;

a pair of handles extending outwardly from opposite sides of the body, the distal ends of the handles each being pivotally connected to the body;

a pair of struts, wherein each strut is pivotally connected to one of the handles;

an axially displaceable actuator mechanism disposed within the body, wherein movement of the handles causes the struts to move which in turn causes axial displacement of the actuator mechanism, wherein, the axially displaceable actuator mechanism controls the opening of a rongeur cutting blade.

2. A control grip assembly, comprising:

a body;

a pair of handles extending outwardly from opposite sides of the body, the distal ends of the handles each being pivotally connected to the body;

a pair of struts, wherein each strut is pivotally connected to one of the handles;

an axially displaceable actuator mechanism disposed within the body, wherein movement of the handles causes the struts to move which in turn causes axial displacement of the actuator mechanism; and a thumb controlled actuator disposed at the distal end of the body.

3. The control grip assembly of claim 2, wherein, the thumb controlled actuator controls the opening of jaws mounted on an articulator.

\* \* \* \* \*